United States Patent [19]

Rubin et al.

[11] 4,401,759

[45] Aug. 30, 1983

[54] DETECTION AND ISOLATION OF GLUCAGON MRNA USING A SYNTHETIC OLIGODEOXYNUCLEOTIDE

[76] Inventors: Harvey Rubin, 2560 First Ave., San Diego, Calif. 92103; Richard H. Tullis, 11180 Roselle St., San Diego, Calif. 92121

[21] Appl. No.: 366,593

[22] Filed: Apr. 8, 1982

Related U.S. Application Data

[63] Continuation-in-part of Ser. No. 145,448, May 1, 1980, abandoned.

[51] Int. Cl.$^3$ .................. C12Q 1/68; C12P 19/34; C12P 21/00; C12N 15/00
[52] U.S. Cl. .................................. 435/91; 435/6; 435/68; 435/172; 536/29; 436/94
[58] Field of Search ............ 435/6, 7, 91, 92, 172, 435/317, 68, 70, 71; 536/29; 436/94

[56] References Cited

U.S. PATENT DOCUMENTS

| | | | |
|---|---|---|---|
| 3,689,475 | 9/1972 | Spiegelman et al. | 435/91 |
| 4,224,408 | 9/1980 | Hung et al. | 435/91 |
| 4,237,224 | 12/1980 | Cohen | 435/68 |
| 4,293,652 | 10/1981 | Cohen | 435/91 |
| 4,321,365 | 3/1982 | Wu et al. | 435/172 |

OTHER PUBLICATIONS

Verma, et al., "Synthesis by Reverse Transcription of DNA Complementary to Globin Messenger RNA", *Chem. Absts.*, vol. 81, No. 13, p. 112 (1974) Abs. No. 73611g.

Ryndich, et al., "Electron Microscopic Study of the DNA in Products of Reverse Transcription", *Chem. Absts.* vol. 91, No. 1, p. 160 (1979), Abs. No. 1500d.

*Primary Examiner*—Thomas G. Wiseman
*Attorney, Agent, or Firm*—Frank D. Gilliam

[57] ABSTRACT

A synthetic oligodeoxynucleotide complementary to glucagon mRNA and a method of using it to detect and isolate glucagon mRNA and cDNA from human and rabbit pancreas. A unique 14 base oligodeoxynucleotide dTTCATCAGCCACTG wherein T represents thymine, G represents guanine, A represents adenine, and C represents cytosine and where at least 13 of the 14 nucleotides are as indicated (one of those indicated may be replaced by one of the other three mentioned nucleotides) has been found to be complementary to glucagon mRNA. To isolate glucagon mRNA, total RNA is first extracted from human or rabbit pancreas and A+ RNA (mRNA-poly A) is isolated from the total RNA. The A+ RNA is then treated with the oligodeoxynucleotide, and the resulting hybridized RNA is enzymatically converted to glucagon mRNA which can then be purified, copied into glucagon cDNA and used in a conventional manner to produce glucagon by cloning technique.

5 Claims, No Drawings

DETECTION AND ISOLATION OF GLUCAGON MRNA USING A SYNTHETIC OLIGODEOXYNUCLEOTIDE

CROSS-REFERENCE TO RELATED APPLICATIONS

This Application is a continuation-in-part of copending U.S. patent application Ser. No. 145,448 filed May 1, 1980 abandoned.

BACKGROUND OF THE INVENTION

This invention relates in general to the isolation of specific ribonucleic acid molecules and, more specifically, to the detection and isolation of glucagon mRNA.

Recently, considerable research effort has been expended in investigating the intricate relationship between genes and proteins. A wide variety of deoxyribonucleic acid (DNA) and ribonucleic acid (RNA) molecules have been detected and have been found to perform a variety of biochemical functions. Some ribonucleic acid polymers have been found to serve a "messenger" function, providing a template guiding definite sequences of amino acids in the assembly of proteins. These messenger RNA (or mRNA) molecules, if detected and isolated, can be used to "manufacture" DNA molecules having the capability of producing selected useful amino acid sequences, such as insulin.

Glucagon is the major polypeptide hormone produced by the alpha cells of the Islets of Langerhans. It is opposite in effect to insulin. Small amounts have been isolated and crystallized, appearing to be a straight chain polypeptide with a molecular weight of about 3500. Glucagon has been found to be useful in the treatment of insulin overdoses, propranol overdoses, insulinoma, heart arrythmias and Von Gherkes disease (an abnormal sugar storage disease). In the future, it may have application in the relief of symptoms of hypoglycemia, the enhancement of wound healing and organ regeneration and as a dieting aid since it speeds fat metabolism.

Presently, no satisfactory method exists for the detection or isolation of reasonable quantities of glucagon mRNA. Thus, there is a continuing need for an improved method for isolating and purifying glucagon mRNA.

SUMMARY OF THE INVENTION

The above problems have been overcome by our method of isolating glucagon mRNA from human and rabbit pancreas using a unique 14 base oligodeoxynucleotide (14 mer). A short segment of the amino acid sequence was used to deduce the sequence of a unique oligodeoxynucleotide complementary to the glucagon mRNA. This oligodeoxynucleotide is then used as a sensitive and specific probe for the glucagon mRNA.

Basically, our method consists of the steps of isolation of human or rabbit pancreas A+ RNA, hybridization with the specific selected oligodeoxynucleotide and enzymatic synthesis of glucagon mRNA which can be copied as glucagon cDNA and subsequently isolated in pure form. This glucagon cDNA can then be used in a conventional manner to produce additional glucagon by recombinant techniques.

DETAILED DESCRIPTION OF THE INVENTION

We have found that certain 14 unit oligodeoxynucleotides may be synthesized which complement the segment of glucagon mRNA coding for the amino acids $^{24}$Gln-$^{25}$Trp-$^{26}$Leu-$^{27}$Met-$^{28}$Asn. These 14-mers will rapidly and specifically hybridize pancreas glucagon A+ RNA (poly A containing mRNA). These 14-mers are specific and sensitive probes for glucagon mRNA sequences in heterogeneous populations of RNA (ribonucleic acid).

The 14-mer used may be any suitable variation in our novel base oligonucleotide. Best results have been obtained with the 14 base oligonucleotide dTTCATCAGCCACTG, which is therefore preferred for use in our purposes. Other typical sequences include: TTCATCAGCCATTG, TTCATCATCCACTG, TTCATCATCCATTG, TTCATTAGCCACTG, TTCATTAGCCATTG, TTCATTATCCACTG, TTCATTATCCATTG, TTCATAAGCCACTG, TTCATAATCCACTG, TTCATAAGCCATTG, TTCATAATCCATTG, TTCATGAGCCACTG, TTCATGAGCCATTG, TTCATGATCCACTG, and TTCATCATCCATTG. Excellent results are obtained so long as at least 13 of the 14 nucleotides are as shown in the preferred arrangement.

Our preferred method for the isolation of glucagon mRNA sequences involves the chemical synthesis of a complementary oligonucleotide deduced from favorable short sequences of amino acids, preferably the 24-28 sequence detailed above. The oligodeoxynucleotide dTTCATCACCCACTG may be prepared in any suitable manner. Typical is the diester approach described by Tu, C.P.D. et al. Anal. Biochem., 74:73–93 (1976).

In this method, selected mono or oligonucleotides are connected one after the other to produce the desired deoxynucleotides. Typically, this process starts with a protected deoxyribonucleotide having as its only free group a 3'hydroxyl to be coupled with a completely protected deoxyribonucleotide. Before condensation begins, the 5' phosphate group of the completely protected deoxyribonucleotide is activated by 2,4,6 tri-isopropylbenzene sulfonyl chloride (TPS). Stepwise synthesis of the desired oligodeoxynucleotide chain is effected by successive condensations involving the 5' end groups of the completely protected deoxyribonucleotides with the 3' hydroxyl of the other deoxyribonucleotides. Our starting material, made by this process, under our direction, was prepared by Collaborative Research, Waltham, MA.

Our first step in our method is the isolation of pancreas A+ RNA from fresh pancreas samples. The characteristics of A+ RNA, also known as mRNA-poly A, are described, for example, on page 339 of "The Biochemistry of the Nucleic Acids", Davidson et al, Academic Press, 1976, ISPN 0412 21380X. The notation A+ RNA refers to mRNA's with a long uninterrupted sequence of adenosine nucleotides attached to at least some of the natural mRNA as a sort of "tail". This "tail" is useful in isolating mRNA, since RNA's with the poly A tail can be more easily separated from other, possibly contaminated, RNA's. Samples of human pancreas islets are obtained from autopsy samples and similarly treated. Total RNA may be obtained by the guanidine hydrochloric acid extraction procedure, preferably using glassware which had been previously baked and treated with diethylpyrocarbonate to remove any traces of RNase. This type of technique is described by R. A. Cox, Metho. Enzymol. 12B:120–129 (1968). A+ RNA may be isolated on oligo-dT-cellulose, using the technique described by J. A. Bantle et. al., in Anal. Biochem. 70:413 (1976). All fractions of RNA are typically assayed for purity and intactness by electrophoresis in 1.5% agarose gels in the presence of 4 mM $Ch_3HgOH$ by the method described by J. M. Bailey et. al., in Anal. Biochem. 70:75 (1976), and for translatability in the wheat embryo in vitro system described by F. B. Johnson et. al. in Nature 179:160 (1957). In vitro translation products may be monitored on sodium lauryl sulfate/9% polyacrylamide gels as described by U. K. Laemmli, Nature 227:680 (1970). The RNA preparations used here in general stimulate the incorporation of $^{35}S$-methionine into large protein products 3 to 5 fold over background.

The radiolabeled 14 mer is then hybridized. Hybridization reactions are typically carried out in a sodium phosphate buffer solution containing about 0.2% sodium lauryl sulfate. Solutions containing about 1 mg pancreas mRNA-polyA and 14 mer ($10^6$ to $10^7$ cpm/ul) may be heated, then cooled to reanneal. The extent of reaction as a function of time may be monitored on an Ultrogel A-44 column (0.7 by 100 cm) in 0.12 M sodium phosphate buffer including about 0.1% sodium lauryl sulfate. The sequence excess of 14 mer to its complement in mRNA is found to be less than or equal to 300:1. The reaction rates may be expressed in terms of equivalent $C_ot$, as described by R. J. Britten, et. al., Methods Enzymol. 29:363 (1974). Control reactions utilizing yeast RNA and rat liver RNA under the same conditions have been found to yield no detectable hybrids, indicating specific hybridization with pancreas glucagon RNA. We estimate the detectable level of glucagon mRNA to be less than 0.1 fmol. Thermal denaturation profile comparisons and comparison of the kinetics of hybridization confirm that the synthetic oligodeoxynucleotide reacts specifically with glucagon mRNA sequences. Thus, a practical method of specific detection and isolation of glucagon mRNA is provided by this invention. As described above, this glucagon mRNA is useful in the production of glucagon cDNA which may be used in conventional cloning procedures to produce glucagon for use in treating the diseases and conditions mentioned above.

While any suitable temperature may be used for the formulation of the hybrids, we have found that if the temperature is too high, there will be little or no capture, while temperatures which are too low tend to produce false captures. While temperatures in the range of from about 0° C. to 80° C. produce useful results, best results are obtained with temperatures in the range of from about 10° to 40° C.

Glucagon mRNA copy DNA (glucagon cDNA) may be produced using the synthetic oligonucleotide as a specific primer by any conventional technique. Briefly, one such conventional method involves the addition of a suitable enzyme and a mixture of thymine, guanine, cytosine and adenine (as their respective deoxynucleotide (triphosphates) to extend the primer, and thus to form glucagon cDNA molecules in accordance with the glucagon messenger RNA "template"; separation of the mRNA from the glucagon cDNA such as by alkaline hydroysis to disperse the RNA, gel electophoresis to isolate the specific glucagon cDNA, cutting out the appropriate band from the electrophoretic gel (as indicated by radioactive tagging, typically), destruction of the agarose gel with sodium perchlorate, which leaves only the desired DNA, which can then be cloned using standard techniques. Thus a practical method for the isolation of glucagon mRNA and glucagon cDNA produced by the method of our invention can be used for other purposes in other methods, as desired.

The cloning techniques used to produce glucagon from glucagon cDNA may be any commonly used procedure such as that which has been used to produce active insulin. Briefly, the method involves enzymatic insertion of glucagon cDNA into a bacterial gene carried on a larger piece of DNA called a plasmid, inclusion of the plasmid into a suitable host bacterium, and subsequent synthesis of the desired protein by the bacterium.

The following examples describe the details of preferred embodiments of our method of isolating glucagon mRNA and of producing glucagon cDNA therefrom. All parts and percentages are by weight, unless otherwise indicated.

EXAMPLE 1

Human pancreas are obtained from brain-dead human cadavers within one hour of death. The pancreatic duct is cannulated and the exocrine pancreas is distended under pressure with cold Hank's solution (in one liter of water: 200 mg calcium chloride, 200 mg hydrous magnesium sulfate, 1273 mg sodium hydrocarbonate, 8000 mg sodium chloride, 100 mg sodium hypophosphate and 2000 mg glucose). The entire pancreas is finely minced with dissecting scissors. The tissue is then digested with collagenase (Worthington Type 4, available from Worthington Chemical Co.), at about 37° C. for about 15 minutes. The resulting suspension of islets is centrifuged for a few minutes at about 200 rpm. The islets are removed by Pasteur pipette and the supernatant is discarded. A small portion of the islets is checked by plating onto a microscope slide under which black paper is placed. When viewed through a low power eyepiece, the islets appear as yellowish-white, roundish bodies. If the islets appear to be in good condition, the process is continued. The balance of the islets are allowed to sediment through percoll in a test tube. Pancreatic digest above the islets is removed by suction and the islets are collected from the bottom of the test tube.

The RNA extraction procedure is then conducted as follows: Each gram of islets are homogenized in about 16 ml. guanidinium thiocyanate stock solution, consisting of 4 M guanidinium thiocyanate, 0.5% sodium dodecyl sulfate (SDS), 0.025 mM sodium citrate, 0.01 M 2-mercaptoethanol and 0.1% Sigma Anti-foam A. Homogenates are centrifuged at about 10° C. to sediment particulate matter. Supernatants are mixed with 0.25 volumes (relative to the original 16 ml/g. homogenate volume) of 1 M acetic acid (to lower the pH to about 5), and 0.75 volume of absolute ethanol. The flask is shaken thoroughly and kept at about −20° C. overnight to precipitate nucleic acid. The material is sedimented by centrifugation for about 10 minutes at about −10° C. and at about 6000 rpm. The tubes are drained of supernatant and any material not forming a firm pellet. Pellets are resuspended in 0.5 volume (relative to the original homogenate volume) of a guanidinium hydrochloride stock solution consisting of about 7.5 M guanidinium hydrochloride, (neutralized to pH 7.0) about 0.025 volume of 1 M sodium citrate and about 5 mM dithioerithritol. RNA is then precipitated by adding, relative to guanidinium hydrochloride volume, about 0.0025 volume 1 M acetic acid and 0.5 volume ethanol. The solution is kept at about −20° C. for at least about 3 hours, then is centrifuged for about 10 minutes at about −10° C. and 6000 rpm. From this point on, all procedures are carried out under sterile conditions to prevent nuclease contamination. The supernatant liquid is removed and the pellets are redispersed in ethanol at room temperature and again centrifuged for about 5 minutes at about 6000 rpm. Residual ethanol is evaporated by a stream of nitrogen and the pellets (now primarily RNA) are dissolved in sterile water. The solution is centrifuged at about 12000 rpm and about 10° C. to sediment insoluble matter. Supernatant is decanted and the insoluble material is reextracted twice by the above method with about 0.5 gram/ml of the original tissue. The combined supernatants are mixed with about 0.1 volume 2 M potassium acetate (pH 5) and about 2 volumes ethanol and left overnight at about −20° C. The RNA is sedimented from the ethanol suspension by centrifugation for about 20 minutes at about 1000 rpm and about −10° C. Pellets are washed with 95% ethanol, dried with nitrogen and dissolved in 1 ml of sterile water per gram starting tissue. The RNA is stored as a 70% ethanol suspension at pH 5 and −20° C. Total RNA is quantified through ultraviolet absorbance measurements in 10 mM triethanolamine hydrochloride, pH 7.4 at a wavelength of 260 nm. The yield of RNA from that present in the original tissue is found to be about 0.5 to 1.0 percent.

Isolation of A+ RNA (mRNA-poly A) from the total RNA is accomplished as follows: Polyadenylated RNA is separated from total RNA through two cycles of binding to oligo d-T cellulose (Type T-3, available from Collaborative Research, Waltham, Mass.). A 0.5 M lithium chloride, 0.2% SDS and 10 mM triethanolamine hydrochloride (pH 7.5) solution is used as the binding buffer. The total RNA samples produced above are heated to about 68° C. to prevent nonspecific ribosomal contamination, then are quickly cooled to about 0° C. and the buffer solution is added. The solution is then applied to the column.

The mRNA extraction is carried out according to the method described by H. Aviv and P. Leder in the Proceedings of the National Academy of Science, 69, 1409 (1972). This oligo (dT) chromatography is carried out at room temperature with glassware and reagents that had been autoclaved with the exception of the oligo (dT) cellulose. Ten A units of islet RNA is dissolved in buffer containing 0.01 M Tris HCL (pH 7.5). About 0.5 M potassium chloride is applied to a 2 ml (about 0.5 g, dry weight) oligo (dT) cellulose column previously washed with the application buffer. The nonabsorbed material is eluted by continued washing with the application buffer. The material retained by the column is eluted in two steps with buffers of reduced ionic strength. The first elution buffer contains about 0.01 M Tris HCL (pH 7.5) and about 0.1 M potassium chloride; the second about 0.01 Tris HCL (pH 7.5). The material eluted in this way is immediately precipitated by the addition of potassium acetate and two volumes of ethanol. The resulting bound mRNA-poly A can be frozen and stored in liquid nitrogen.

The purity of the isolated mRNA-poly A is analyzed as follows before proceeding with the process: The mRNA-polyA produced above is subjected to gel electrophoresis in a 3% agrose, 40 mM Tris buffer, 20 mM sodium acetate, 2 mM ethylenediaminetetraacetic acid (EDTA) solution at pH 7.4. This solution is prepared by dissolving agarose in sterile water while held over a flame, then swirling thereinto the other ingredients. This solution is immediately poured into a pre-narrowed mold, about 150 mm by 100 mm by 2 mm. The resulting gel is allowed to cure for about 1 hour at about 4° C. The gel is then preelectrophoresed for about one-half hour at about 100 v/16 mA with 1x of the Tris/acetate/EDTA solution described above as a reservoir buffer. Samples are applied in 3 microgram aliquots and electrophoresed against known markers for about 4 hours at about 100 v/16 mA. The gels are fixed in 7% acetic acid for about 20 minutes, stained in 0.2% methylene blue in 0.5 M sodium acetate/0.4 M acetic acid (pH 7.4) for about 8 hours and destained in water. The RNA samples are tested for biological activity by translation in rabbit reticulocyte lysate systems, supplied by BRL Labs. A 30 microliter reaction mixture consists of about 10 microliter reticulocyte lysate (about 3.5 mM magnesium chloride, about 0.05 mM EDTA, about 25 mM potassium chloride, about 0.5 mM dithioerethreitol, about 25 mM hemin, about 50 microgram/microliter creatine kinase, about 1 mM calcium chloride, about 2 mM EGTA and about 70 mM sodium chloride), about 3 microliter protein biosynthesis reaction mix (about 250 mM HEPES, about 400 mM potassium chloride, about 100 mM creatine phosphate, 19 amino acids at about 500 mM each, about 0.7 microliters sterile water and bout 5 microliters 3H leucine) and about 10 microliters mRNA (0.1 microgram/microliter). Reaction mixes are incubated for about 1 hour at about 30 degrees and then placed on ice. An aliquot, about 10 microliters, is spotted on a glass fiber filter which is then boiled for about 10 minutes in 10% trichloracetic acid (TCA) to hydrolize charged tRNA. The filters are washed in cold TCA and with ethanol, air dried and counted in a toluene based scintillation fluid. The in vitro translation products are then analyzed. About 5% agarose gels are prepared analogous to the RNA gels except that 10x SDS/sodium phosphate buffer (0.286 M monobasic sodium phosphate, 0.714 moles dibasic sodium phosphate, 10 g. SDS are mixed in 1 liter of sterile water, giving a final pH of 7.2) is used as the gel buffer. The electrophoresis is carried out for one hour at 200 v/39 mA. Protein samples are incubated in a solution of about 0.01 M sodium phosphate, about 1% SDS, about 1% beta-mercaptoethanol at a pH of 7.0, in a boiling water bath for about 5 minutes, then are immediately put on ice. The gels are fixed for about 20 minutes in 5% TCA, sample lanes are cut into mm slices, dissolved in about 10 microliters of scintillation fluid and counted. The results of the count are 60,000–80,000 cpm/microgram mRNA (glucagon).

The next step is to isolate glucagon mRNA specifically. This is accomplished by utilizing a novel synthetic oligodeoxynucleotide probe designed to hybridize specifically with glucagon mRNA. The radiolabeled nucleotide sequence dTTCATCAGC-CCACTG as conceived by us was prepared under our direction by Collaborative Research. Collaborative Research used known diester techniques as described above to assemble this nucleotide sequence. Hybridization reactions are carried out in about 0.5 M sodium phosphate (about 0.245 M dibasic sodium phosphate, about 0.255 M monosodium phosphate and about 2% SDS at a pH of about 6.8 and about 23° C. An about 0.5 microliter solution containing about 0.5 micrograms mRNA-poly A and 14-mer (the above nucleotide), giving about 10⁶cpm/reaction, is heated for about 2 minutes, then cooled to about 20° C. to allow reannealing to take place. Reaction mixes are then layered onto about 20% sucrose gradients and centrifuged for about 10 hours at about 41000 rpm to separate hybridization products. The radioactive glucagon mRNA-poly A oligodeoxynucleotide hybrid band is aspirated. Control reactions utilizing yeast and rat liver RNA under the same conditions yield no detectable hybrids, indicating hybridization only with glucagon mRNA. The amount of glucagon mRNA as judged by hybridization is found to be in the range of about 1 to 5 percent of that in the original samples of mRNA poly A.

Glucagon cDNA (mRNA-poly A copy DNA) is then produced using the method generally described by Leis and Hurwitz in Methods of Enzymology, 1974, 29,143. We utilize the synthetic oligodeoxynucleotide glucagon mRNA hybrid as a template primer complex. The reaction mixture, about 0.05 ml consists of about 1 microliter Tris (1.0 M, pH 8.0), about 5 microliter magnesium chloride (0.1 M), about 2 microliters dithioerithritol (0.15 mM), about 1 microliter potassium chloride (0.25 M), about 5 microliters each of d-ATP, d-GTP, d-CTP (a mM each), about 5 microliters H3 d-TTP (0.2 mM), about 10 microliters glucagon mRNA hybrid complex (10 O.D./ml), about 10 microliters reverse transcriptase (500 units/ml) and water. The reaction is allowed to proceed for about 30 minutes at about 38° C. An aliquot is taken and applied to a glass fiber filter, dried by heat and counted in 10 ml toluene-based scintillation fluid. Reaction mixes lacking enzyme or template are also prepared to serve as controls. The actual reaction mixture is mixed with 2 volumes of ethanol to precipitate the product. This mixture is chilled to −20° C. overnight. The precipitate is collected by centrifugation at 10000 rpm for about 20 minutes. The resulting pellet is then dissolved in about 0.3 M sodium hydroxide (0.3 N) and incubated at about 37° C. for about 16 hours to hydrolize RNA. The mix is made 0.3 M with sodium chloride and is precipitated in about 2 volumes ethanol, chilled overnight and sedimented by centrifugation as described just above. The resulting cDNA is then applied to 0.8% agarose in Tris/acetate/EDTA pH 8.0 buffer as described previously with the RNA electrophoresis. The portion of the gel containing radioactivity is then sliced out and incubated in an about 50° C. water bath until the gel is fluid. An equal volume of phenol/-chloroform is added to the extract glucagon cDNA. The aqueous phase is adjusted to 0.3 M sodium acetate and the H3 labeled cDNA is precipitated by the addition of 2.5 volumes of ethanol. Ethanol is blown off with a stream of nitrogen gas and the DNA is finally dissolved in a solution of 0.15 M sodium chloride and 0.015 M sodium citrate. The solution is centrifuged at 130,000 rpm for about 1 hour at about 5° C. The clear solution is kept at about 2° C. over chloroform. The solution is analyzed and the yield of glucagon cDNA is found to be about 10–40% of starting mRNA (glucagon). The glucagon cDNA is suitable for cloning by conventional techniques.

EXAMPLES 2-17

The process described in Example 1 is repeated, with all process steps performed in a substantially identical manner, except that in place of the 14 base oligodioxynucleotide (14-mer) dTTCATCAGCCACTG, the following 14-mers are used:

TTCATCAGCCATTG, TTCATCATCCACTG, TTCATCATCCATTG, TTCATTAGCCACTG, TTCATTAGCCATTG, TTCATTATCCACTG, TTCATTATCCATTG, TTCATAAGCCACTG, TTCATAATCCACTG, TTCATAAGCCATTG, TTCATAATCCATTG, TTCATGAGCCACTG, TTCATGAGCCATTG, TTCATGATCCACTG, and TTCATGATCCATTG.

In each case, identification of glucagon mRNA is achieved. However, in these examples, yields are lower than with the 14-mer of Example 1.

EXAMPLES 18-19

The process of Example 1 is repeated except that fresh rabbit pancreas is used in place of human pancreas and the 14-mer sequence is TTCATCAGCCACTG for Example 18 and TTCATGATCCATTG for Example 19. Excellent yields of glucagon mRNA are obtained.

EXAMPLES 20-27

The process of Example 1 is repeated with all of the process conditions and steps substantially the same except that the temperature of the hybridization step is varied as follows: Example 20 at −10° C., Example 21 at 0° C., Example 22 at 10° C., Example 23 at about 30° C., Example 24 at about 40° C., Example 25 at about 60° C., Example 26 at about 80° C., and Example 27 at about 100° C. Optimum results are obtained in the range from about 10° to 40° C. Higher temperatures produce lower capture rates, while lower temperatures result in false captures and contamination of the product.

Other ramifications, applications and variations of this invention will occur to those skilled in the art upon reading this disclosure. These are intended to be included within the scope of this invention, as defined in the appended claims.

We claim:

1. The method of isolating glucagon mRNA from human and rabbit pancreas which comprises the steps of:
    extracting total RNA from rabbit or human pancreas;
    isolating mRNA-poly A from said total RNA; and
    hybridizing said mRNA-poly A with a 14 base oligodeoxynucleotide dTTCATCAGCCACTG, wherein A represents adenine, T represents thymine, G represents guanine and C represents cytosine, and wherein at least 13 of the 14 nucleotides are as indicated.

2. The method according to claim 1 wherein said hybridization temperature range is from about 0° to 50° C.

3. The method according to claim 1 further including the steps of copying said hybridized mRNA into complementary DNA and isolating said complementary DNA whereby substantially only cDNA resulting from glucagon mRNA remains.

4. The method of isolating glucagon mRNA from human pancreas which comprises the steps of:
    separating pancreas islets from fresh human pancreas;
    extracting total RNA from said islets by guanidine hydrochloric acid extraction;
    isolating mRNA-poly A from said total RNA on oligo-dT-cellulose;
    hybridizing said mRNA-poly A in a sodium phosphate buffer with the 14 base oligodeoxynucleotide dTTCATCAGCCAACTG, wherein A represents adenine, T represents thymine, G represents guanine and C represents cytosine, and wherein at least 13 of the 14 nucleotides are as indicated.

5. The method according to claim 4 further including the step of analyzing the isolated mRNA-poly A prior to hybridizing said mRNA-poly A.

* * * * *